(12) United States Patent
Wang et al.

(10) Patent No.: US 7,981,928 B2
(45) Date of Patent: Jul. 19, 2011

(54) CHEMOTHERAPY METHOD USING X-RAYS

(75) Inventors: Chia-Gee Wang, Millwood, NY (US); Lawrence Helson, Quakertown, PA (US)

(73) Assignee: Nanodynamics, Inc., New York, NY (US)

( * ) Notice: Subject to any disclaimer, the term of this patent is extended or adjusted under 35 U.S.C. 154(b) by 202 days.

(21) Appl. No.: 10/651,307

(22) Filed: Aug. 28, 2003

(65) Prior Publication Data
US 2004/0259811 A1    Dec. 23, 2004

Related U.S. Application Data

(60) Provisional application No. 60/408,313, filed on Sep. 5, 2002.

(51) Int. Cl.
*A61K 31/35* (2006.01)
(52) U.S. Cl. ...................................................... 514/454
(58) Field of Classification Search .................. 600/431; 378/65; 514/454, 310
See application file for complete search history.

(56) References Cited

U.S. PATENT DOCUMENTS

| | | | |
|---|---|---|---|
| 5,044,001 A | 8/1991 | Wang | 378/43 |
| 5,627,871 A | 5/1997 | Wang | 378/121 |
| 5,641,764 A | 6/1997 | Martin et al. | 514/80 |
| 5,675,025 A | 10/1997 | Sisti et al. | 549/510 |
| 5,688,977 A | 11/1997 | Sisti et al. | 549/510 |
| 5,776,925 A | 7/1998 | Young et al. | |
| 5,859,065 A | 1/1999 | Brandes | 514/651 |
| 5,994,409 A | 11/1999 | Stogniew et al. | |
| 6,191,290 B1 | 2/2001 | Safavy | 549/510 |
| 6,224,848 B1 | 5/2001 | Mills | 424/1.65 |
| 6,307,088 B1 | 10/2001 | Swindell et al. | 560/27 |
| 6,331,286 B1 * | 12/2001 | Dees et al. | 424/1.85 |
| 6,366,801 B1 | 4/2002 | Cash, Jr. et al. | 600/431 |

FOREIGN PATENT DOCUMENTS

WO    WO 00/37927    *    6/2000

OTHER PUBLICATIONS

Ariel et al., "Treatment of Inoperable Cancer of the Liver by Intra-Arterial Radioactive Isotpes and Chemotherapy", Cancer, vol. 20, No. 5, pp. 793-804 (May 1967).*
Goldman et al., Cecil Textbook of Medicine, 21st Edition, pp. 1060-1074 (2000).*
Larson, D. et al. "Auger Electron Contribution to Bromodeoxyuridine Cellular Radiosensitization." *International Journal of Radiation Oncology •Biology• Physics*, (1989) 16(1), pp. 171-176.
Mills, Randell L. et al. "A novel cancer therapy using a Mössbauer-isotope compound." *Nature*, (1988) vol. 336, pp. 787-789.
Laster, B.H. et al. "Photon Activation of Iododeoxyuridine: Biological Efficacy of Auger Electrons." *Radiation Research: An International Journal*, (1993) 133, pp. 219-224.

* cited by examiner

*Primary Examiner* — James D Anderson
(74) *Attorney, Agent, or Firm* — Ladas & Parry LLP

(57) ABSTRACT

A method of treating cancer in a human uses x-rays to disrupt a linkage in a complex of a chemotherapeutic agent and a carrier compound comprising a pre-selected element. The complex is administered to the human and then a localized region of cells which contains the cancerous cells is irradiated with line emission x-rays of an energy selected to cause emission of Auger electrons from the pre-selected element of the carrier compound to disrupt the linkage and release the chemotherapeutic agent near the cancer cells. A kit useful for the treatment comprises an x-ray tube capable of emitting monochromatic line emission x-rays and the complex compound. A transfer compound useful in the method comprises a chemotherapeutic agent linked to a carrier compound.

20 Claims, 6 Drawing Sheets

The Emission Spectrum of an End-Window Moly Target

The emmision spectrum of an end-window Ag target

CHEMOTHERAPY METHOD USING X-RAYS

CROSS-REFERENCES TO RELATED APPLICATIONS

This application claims the benefit of U.S. Provisional Application No. 60/408,313, filed Sep. 5, 2002.

BACKGROUND OF THE INVENTION

1. Field of the Invention

The present invention relates to treatment of cancer and other tumors in humans, in which x-rays are used to deliver a chemotherapeutic compound in proximity to cancer cells. The invention also relates to a kit useful for such treating; and to compounds, complexes and compositions useful for such treating.

2. Description of the Related Art

In the United States, there are two million new cancer cases each year. About 600,000 patients undergo radiation therapy and almost two million undergo chemotherapy at a cost of well over $100 billion. Both of these therapeutic approaches rely on the increased sensitivity of rapidly dividing cancerous cells to toxic agents. Since the toxic agent is often supplied to the whole body and many normal body tissues are also dividing rapidly (hair roots, cells of the gut lining, etc.) a balance must be achieved between killing the maximum number of cancerous cells while doing the minimum damage to normal body cells. Considerable effort has been made either to maximize this discrimination or to target the toxic agent specifically to the tumor cells. The approach of the invention is designed to overcome the drawbacks inherent in radio- and chemotherapy by using localized delivery of x-rays to activate a compound comprising a chemotherapeutic compound linked to a complex containing an element that can generate ionizing radiation which will disrupt the linkage and release the chemotherapeutic compound. Compounds comprising such elements can be given to the whole body and only activated in the region of the tumor by a narrow, focused beam of specific energy x-rays, to release the chemotherapeutic compound.

Efforts to selectively target cancer cells are disclosed in prior art such as U.S. Pat. No. 5,859,065 which discloses improved therapy by first treating the subject with a compound that inhibits normal cell proliferation while promoting malignant cell proliferation, and then treating with a chemotherapeutic agent; and in U.S. Pat No. 6,366,801 which discloses using compounds having heavy elements to enhance the radiotherapy dose ratio of tumor dose to normal tissue dose. A ratio of up to 10:1 is claimed to be achieved.

U.S. Pat. No. 5,641,764 discloses using halogenated DNA ligands to induce radiation damage in DNA in response to ionizing or ultraviolet (UV) radiation. An iodinated ligand was found to sensitize cell destruction by UV exposure, and the inventors speculate that the ligands may also act as sensitizers of ionizing radiation (from radioactive nuclei or from x-rays).

U.S. Pat. No. 6,224,848 discloses a method of cancer therapy. A compound which binds to the target tissue and contains a gamma radiation absorber isotope is administered. The bound compound is excited by an apparatus using a radiation source consisting of a radioactive isotope or a synchrotron, to release resonant gamma radiation. The gamma radiation is converted internally by the isotope at the target tissue into particle radiation followed by an Auger cascade which is said to damage DNA. Disadvantages of use of a synchrotron source are discussed hereinafter in a section headed "Functional X-Rays".

An x-ray apparatus in which an e-beam is generated in a tubular chamber and focused on a thin metal foil supported inside the chamber on an end window transparent to x-rays is described in the present applicant's U.S. Pat. No. 5,044,001, the disclosure of which is incorporated herein by reference.

A compact end window, transmission x-ray tube assembly suitable for use in the present invention is disclosed in the present applicant's U.S. Pat. No. 5,627,871, the disclosure of which is incorporated herein by reference. In this x-ray tube, the composition of a thin metal foil target and the energy of an e-beam are selected to generate a microfocused bright beam of x-rays of a pre-selected energy.

Methods for producing taxol and taxol analogs are disclosed, e.g., in U.S. Pat. Nos. 5,675,025, 5,688,977 and 6,307,088.

U.S. Pat. No. 6,191,290 discloses derivatives of taxanes such as paclitaxel (taxol) and taxol analogs conjugated to a receptor ligand peptide, forming a tumor-recognizing conjugate.

SUMMARY OF THE INVENTION

In accordance with one embodiment of the invention there is provided a method of treating tumors or cancer in a human in need of such treatment, which comprises the steps of: (a) administering to the human a compound comprising a pre-selected element; and then (b) irradiating a selected region, in which tumorous or cancerous cells are located, with line emission x-rays of an energy selected to cause emission of Auger electrons from said pre-selected element in a dose effective to disrupt intracellular components of said tumorous or cancerous cells, wherein said compound is rose bengal and said intracellular components are lysosomes.

The method of the invention utilizes the emission of Auger electrons from elements, particularly heavy elements, that have been irradiated with x-rays, particularly monoenergetic x-rays tuned to the K-absorption edge of the element. These electrons can deliver concentrated dosages of ionizing radiation of more than $10^6$ gray (Gy) per activation to localized areas only a few atomic diameters across. By "activation" is meant each separate irradiation when more than one is done. In one embodiment, a carrier compound or complex is linked to a chemotherapeutic compound by a bond or a bridging molecule, the resulting linked substance being called herein a transfer compound. The element which can emit ionizing radiation is bound or coupled to the carrier compound, the bridging molecule or the chemotherapeutic compound. Upon administration to a human, the transfer compound will be brought into the vicinity of normal cells and cancer cells. Irradiation of the emitter elements in the locality of a tumor will release Auger electrons resulting in breaking the linkage to the chemotherapeutic compound, thus releasing the chemotherapeutic compound in the vicinity of the tumor and in proximity to the cancerous cells. Transfer compounds which are substantially non-toxic are advantageous since they can be administered throughout the body, without needing to be selective for, or having an affinity to, specific organs or tissues. The substantially non-toxic transfer compounds can be given at whole body dosages and will not be activated until illuminated with x-rays of the appropriate energies. The term "whole body dosage" herein means a dosage which may be distributed through the body and may be given up to the maximum dosage tolerated, i.e. without causing unacceptable toxicity or collateral damage to non-cancerous tissue.

The x-ray beam provides the ability to localize the release of Auger electrons to eliminate cancerous or tumorous cells with minimum damage to other normal body tissues. A number of transfer compounds will meet the criteria for low or no toxicity. Compounds having higher toxicity also may be used, e.g. at lower dosages or when the compounds have an affinity for cancerous tissue.

An example of a transfer compound contemplated herein is a taxane linked or conjugated to a ligand such as a chelate comprising gadolinium. Many other chemotherapeutic agents may be used as part of the transfer compound. In the United States, there are more than 95 FDA approved chemotherapeutic agents, and it is believed that many of them can be incorporated into a Gd-based transfer compound.

According to the invention there is provided a method of treating tumors or cancer in a human in need of such treatment, which comprises:
  (a) administering to the human a transfer compound which comprises a chemotherapeutic compound linked to a carrier compound by a bond or a bridging molecule, said carrier compound, bridging molecule or chemotherapeutic compound comprising a pre-selected element; and then
  (b) irradiating a selected region, in which tumorous or cancerous cells are located, with line emission x-rays of an energy selected to cause emission of Auger electrons from said pre-selected element in a dose effective to disrupt the linkage to said chemotherapeutic compound and thereby release said chemotherapeutic compound in proximity to said cancerous cells.

Further provided according to the invention is a method of treating cancer in a human in need of such treatment, which comprises:
  (a) administering to the human a transfer compound which comprises a chemotherapeutic compound linked to a carrier compound by a bond or a bridging molecule, said carrier compound, bridging molecule or chemotherapeutic compound comprising a pre-selected element selected from the group consisting of Br, Ru, I, Gd and Pt; and then
  (b) irradiating at least once, by means of an end window transmission x-ray tube, a selected region, in which cancerous cells are located, with line emission x-rays of an energy selected to cause emission of Auger electrons from said pre-selected element in a dose effective to disrupt the linkage to said chemotherapeutic compound and thereby release said chemotherapeutic compound in proximity to said cancerous cells, said dose for each activation of said x-ray tube being at least about $10^6$ Gy within a distance from the pre-selected element of the carrier compound of up to about 10 angstroms.

Still further provided according to the invention is a kit for treating tumors or cancer in a human, which comprises:
  (1) an x-ray tube having a target comprising a selected metal, said tube being capable of emitting monochromatic line emission x-rays; and
  (2) a transfer compound which comprises a chemotherapeutic compound linked to a carrier compound by a bond or a bridging molecule, said carrier compound, bridging molecule or chemotherapeutic compound comprising a selected element, the selected metal of said target and the selected element of said transfer compound being selected together:
    (a) for said metal of said target to emit line emission x-rays having an energy above and near the K-absorption edge or the L-absorption edge of the selected element of said transfer compound; and
    (b) for said selected element of said transfer compound to release a dose of Auger electrons upon irradiation by said line emission x-rays.

Also further provided according to the invention is a transfer compound for use in treating cancer or tumors in a human, which comprises:
  a chemotherapeutic compound linked to a carrier compound by a bond or bridging molecule, said carrier compound, bridging molecule or chemotherapeutic compound comprising a pre-selected element; said pre-selected element being capable, when irradiated with line emission x-rays having a selected energy, of emitting Auger electrons in a dose effective to disrupt the linkage to said chemotherapeutic compound.

DETAILED DESCRIPTION OF THE INVENTION

Figure 1:
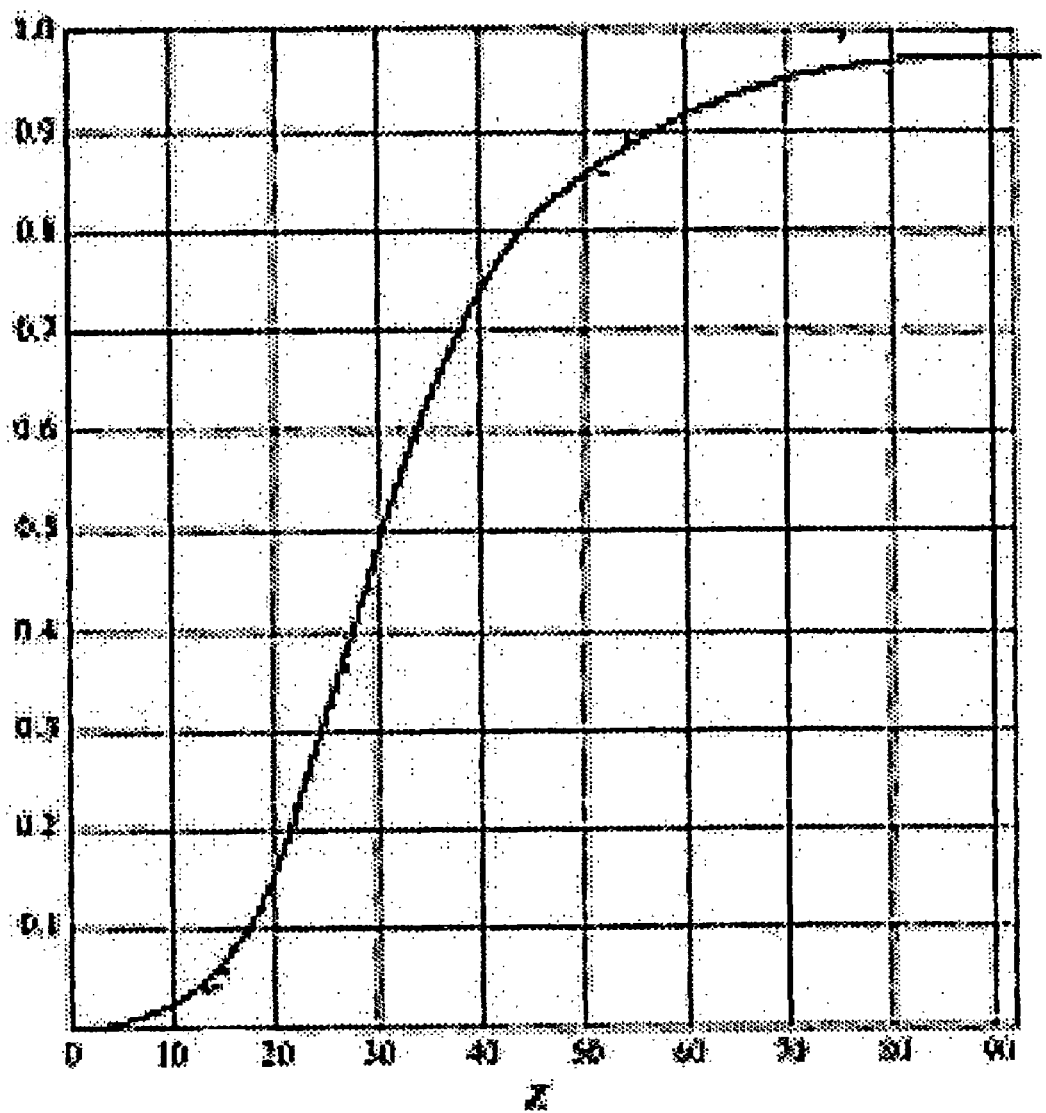
FIG. 1 is a graphical illustration of the relation between the fraction of energy emitted as fluorescent photons upon inner shell ionization and atomic number.

The key component of the method of the invention is the ability to produce bright x-ray beams of defined line emissions. Traditionally, this could be done using synchrotron radiation but in this case, the brightness of the photon flux drops by $E^{-4}$ (where E is the photon beam energy) and as a result is virtually useless at x-ray photon energies greater than 20 kV, well below the energy needed for the heavy element triggers to be used. X-ray tubes, in contrast, provide a photon flux that increases by $E^{1.7}$ with increasing electron beam energy. But traditional x-ray tubes produce largely Bremsstrahlung or slow-down radiation, and do not provide the required specific line emissions. In the present invention, a linear x-ray tube is used which produces largely line emissions where the energy of the emission lines can be selected by selecting the metal element used for the target. Appropriate targets can then be used to give x-ray line emissions tuned to the absorption edge of the elements which will emit Auger electrons.

Chemotherapy is well known for its side effects, and a great deal of effort has been spent to reduce the side effects of the whole body treatment. Radiation therapy, on the other hand, can deliver topical treatment, but the treatment is generally not sensitive to the metabolic uptake of the targeted tissues. If the topical delivery of radiation can be combined with the cellular uptake of therapeutic agents, it brings about indeed a powerful tool for cancer treatment. Herein, this therapy uses a novel tool, a "functional x-ray", where x-rays with monochromatic line-emissions are used to trigger the emission of Auger electrons in situ. These low energy Auger electrons with their total ionization energy transferred within a few atomic distances, provide a dose at $10^6$ Gy or higher, and thereby produce the desired disruption of the linkage to the chemotherapeutic agent in the transfer compound.

The therapeutic effect will be delivered directly to the cancer cells at the targeted tumor-bearing site. The aim is to drastically reduce the exposure of toxicity to the body's healthy organs or tissues.

In the method of the invention, a transfer compound comprising a chemotherapeutic or antineoplastic compound linked by a bond or a bridging molecule to a carrier compound, the transfer compound comprising a pre-selected element, is administered to a human. The bond may be a covalent bond, and the bridging molecule may be a molecule capable of covalent bonding to the chemotherapeutic agent and to the carrier compound, e.g., may be a divalent organic molecule. The compound may be administered to the human for treatment of the human or for treatment of removed tissues or organs. Administering the compound also is meant to include administering it directly to removed tissues or organs. Tissues or organs removed from the body may be removed for purposes such as transplanting, e.g. bone marrow, or for treatment outside the body and subsequent return to the body.

The administered compound may have an affinity for both normal and cancerous cells. Therefore, it is preferred for the compound to be substantially non-toxic. By "substantially non-toxic" it is meant that the administered compound does not cause harmful or life-threatening damage to normal tissue and organs of the mammal in doses effective for accomplishing the irradiation step of the method of the invention. The use of compounds which are substantially non-toxic facilitates administration of a whole body dose of the compound. Administration of a whole body dose without serious effect on normal tissue is especially advantageous due to reducing or avoiding side-effects and enabling simple means of administration.

However, transfer compounds which have some toxic effect, also may be used. In using such compounds it is preferred that they have a selective affinity for cancer cells, i.e. that such compounds be taken up more by cancerous cells, or organs comprising cancerous cells, than by normal cells or organs. For example, the carrier compound portion of the transfer compound may have an affinity for cancer cells. Another way of using transfer compounds having some toxic effect is by direct application to the tissue to be treated, and carrying out the irradiation step soon after application. Alternatively, compounds which have more of a toxic effect may be used in a dosage which is low enough to avoid serious side effects, but is sufficient to accomplish the treatment enabled by the irradiation step of the invention.

The element, i.e. pre-selected element, of the transfer compound is an element which will emit Auger electrons in a dose effective to disrupt the linkage in the transfer compound to the chemotherapeutic compound upon being irradiated by line emission x-rays of an energy selected to cause the emission of Auger electrons from the pre-selected element.

Preferably, the pre-selected element of the compound will have an atomic number (Z) in the range of from 35 to 79. More preferably, Z will be from 44 to 78. In this range, preferred elements are the heavy elements Ru, I and Gd. Lighter elements such as bromine may be used for some treatments. The use of lighter elements, however, is limited as more fully described below because the line emission x-ray energy needed to trigger the emission of Auger electrons is relatively low compared to the energy required for the heavy elements. As a result of the lower energy used, tissue penetration by the line emission x-rays is low. Consequently, lighter elements such as Br may be used for treatments where the cancerous cells are superficial, for instance, in treatment of melanoma.

To minimize any potential toxic effects preferably the transfer compound, the bridging molecule and the carrier compound are selected to have a high rate of excretion by normal physiological processes. For the same reason, it is preferred that the transfer compound, the bridging molecule and the carrier compound should be selected for stability against dissociation of the pre-selected element during the time prior to substantially complete excretion or metabolism of the transfer compound and of the carrier compound released when the transfer compound is irradiated.

The transfer compound may be administered in any way that is effective for bringing it into contact with the tumor or the cancer cells. The transfer compound may be administered orally, enterically, intravenously, topically, or by injection. In most cases administration will be done intravenously. Depending on the properties of the compound, oral administration may be used. In addition, administration can be selectively directed to specific organs or tissues containing cancerous cells, e.g. by direct injection or by selecting compounds having an affinity to the cells, organs or tissues to be treated. The dose of the compound is dependent on the human being treated and on both the transfer compound and the chemotherapeutic agent component being used. In most instances, a whole body dose can be administered in an amount effective to bring the transfer compound into close relationship with cancerous cells, such dose being substantially non-toxic to the normal cells.

As discussed more fully hereinbelow, the line emission x-rays required in the method of the present invention preferably are generated by use of an end window transmission x-ray tube which can produce bright line emission x-rays. A preferred x-ray tube employs an e-beam in the tube which is focused on a thin target having a thickness of up to about 40 µm, said target being inside the tube and coated on or functioning as part of the end window. Both the target and the e-beam energy are selected to provide substantially monochromatic line emission x-rays having an energy above and near the K-absorption edge or the L-absorption edge of the pre-selected element of the compound. Preferably, the thin target is selected from the metal or metallic elements Rb, Mo, Ag, La, Sr and Tm.

By selection of the pre-selected element of the compound and the characteristics of the x-ray tube, a specific energy of line emission x-rays can be selectively employed to result in irradiation of the pre-selected element causing Auger electrons to be released with a dose of at least about $10^6$ Gy. This dose is most effectively released within a distance from the pre-selected element of the transfer compound of up to about 10 angstroms.

The irradiation step, i.e. activation, of the pre-selected element to cause release of Auger electrons may be done only once for effective treatment. The activation can, however, be repeated one or more times. In the first activation as well as in each repeated activation, a dose of at least about $10^6$ Gy may be released.

In the method of the invention, the irradiation provided by line emission x-rays is directed to a localized region of cells which contains or which predominantly contains cancerous cells, to localize the effect of releasing the chemotherapeutic compound to the cancerous cells and minimize the effect on normal cells.

The irradiation may be directed by CT or MRI image guided delivery systems, which are well known for radiotherapy.

The Generation of Auger Electrons

When an atom undergoes an inner shell ionization, either by scattering with a photon or electron, or by a K-capture where a proton from the nucleus captures a K-electron and forms a neutron, which reduces the number of charges Z in the nucleus by one unit and the atom becomes a (Z minus 1) chemical element, the atom undergoes either a fluorescence or a radiationless transition. All x-rays, fluorescent or otherwise, deliver their ionizing radiation initially through the generation of photons and electrons. FIG. 1 shows the fluorescence yield, as a fraction of the total yield plotted against Z. It can be seen that the fluorescence yield when Z is the atomic number for iodine is 90%, for Br is 62%, and for Ti is 20%. The radiationless transition involves for example the L-electron dropping to K, but the transition energy being absorbed by another L-electron which uses it to leave the atom, thus creating two L-shell ionizations, which in turn, allows two M-electrons to drop to the L-shell, and the transition energies being used to allow two M-electrons to leave the atom, creating 4 M-shell ionizations, etc. In short, the radiationless transition, the "Auger series" or "Auger cascade", produces a string of soft ionizing electrons typically at 14-18 eV each, all initiated from a single inner shell (mostly K) ionization. For light atoms such as titanium, the Auger yield (at 80% as against the fluorescence yield at 20%) is very high, but each Auger cascade would produce only a few electrons, whereas heavy atoms such as iodine, have only a 10% Auger yield, but produce many more Auger electrons per each event, the total Auger doses being approximately of the same order of magnitude for these two elements.

Figure 2:
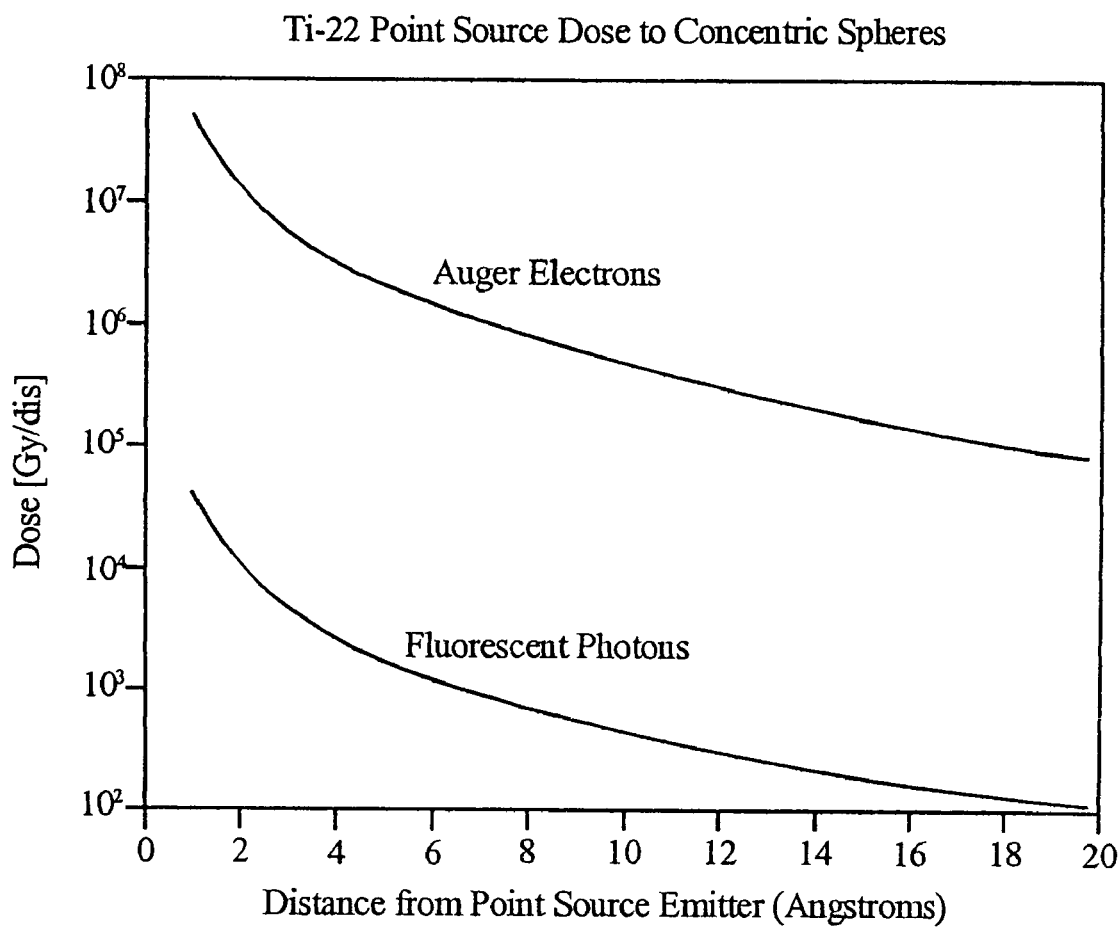
FIG. 2 is a graphical illustration of the relation between the dose of emitted radiation and the distance from the emitter.

Table 1 provides a detailed calculation of the titanium transition states, with each possible transition probability included. FIG. 2 illustrates the radiation dose (in water) of Auger electrons as well as the total photon dose. For titanium, Z is low and the photons are relatively soft, yet the electron dose is already more than 3 orders of magnitude higher than the photon dose at small distances. For iodine, the fluorescent photons at 30 kV are much harder, yielding a much smaller LET (linear energy transfer), thus giving rise to a higher electron/photon dose ratio even though the fluorescent yield for iodine is 90%, as shown in FIG. 1.

TABLE 1

| Properties | Element | |
|---|---|---|
| | Titanium | Calcium |
| Atomic Number (Z) | 22 | 20 |
| K-shell Energy (keV) | 4.966 | 4.038 |
| Fluorescent, Auger Yield | 0.22, 0.78 | 0.16, 0.84 |
| Energy, Range of Primary Auger | ≈16 eV, 9 Å | ≈16 eV, 9 Å |

The Predicted Auger for Titanium

| Transition | Probability | Energy (keV) | Range (Å) |
|---|---|---|---|
| | | | X-rays |
| K-Shell Auger Electrons | 0.22 | 4.96 | ≈1 × 10$^6$ |
| $KL_1L_1$ | 0.004 | 4.17 | 6190 |
| $KL_1L_2$ | 0.017 | 4.26 | 6410 |
| $KL_1L_3$ | 0.004 | 4.29 | 6500 |
| $KL_2L_2$ | 0.005 | 4.36 | 6670 |

TABLE 1-continued

| $KL_2L_3$ | 0.047 | 4.38 | 6720 |
|---|---|---|---|
| $KL_3L_3$ | 0.004 | 4.40 | 6760 |
| $KL_1X$ | 0.005 | 4.80 | 7810 |
| $KL_2X$ | 0.004 | 4.90 | 8100 |
| $KL_3X$ | 0.007 | 4.91 | 8120 |
| KXY | 0.001 | 5.39 | 9470 |
| $L_1MM$ | 0.002 | 0.60 | 335 |
| $L_2MM$ | 0.038 | 0.49 | 259 |
| $L_3MM$ | 0.179 | 0.48 | 253 |
| MXY | 0.463 | 0.016 | 8.9 |

An investigation of a method called "nuclear chemotherapy" was done many years previously at Sloan-Kettering Research Institute in New York, by Dr. Chia-Gee Wang and Dr. Lawrence Helson. The research was done using $^{77}$BrdC, where $^{77}$Br (half-life at 57 hours) would undergo a K-capture and deliver 10$^6$ or more Gy at a small distance. The oxidation of BrdC to BrdU can be blocked by the non-toxic $H_4U$ and therefore excluding BrdC from being incorporated into the DNA pool. Certain transformed cells, on the other hand, would make use of a more primitive kinase to bypass the $H_4U$ blockage, and incorporate BrdC to form BrdU. The $^{77}$Br was made by adding an α particle to $^{75}$As in a facility in the U.K. $^{77}$Br was obtained in liquid solution, and $^{77}$BrdC was made. Of the ten neuroblastoma lines tested; two of the ten lines were sensitive to such an attack. Treating the sensitive tumor lines, in fact, does not cause the cell death immediately. The cells simply stopped mitosis while continuing most of the cellular functions. The Auger electrons from the $^{77}$BrdU delivered such a high dose of the DNA duplex that no cellular repair was possible. This shows that the high ionizing dose is exceedingly localized, and would not harm the cell if the BrdC molecule is not incorporated into the DNA pool, as evidenced by the 8 non-sensitive lines of the 10 neuroblastoma lines to which $^{77}$BrdC was administered, and some doses of the $^{77}$BrdC were at a level a few orders of magnitude higher than those used for sensitive lines.

The inner shell ionization of Br can be initiated by a K-capture or by a photon with energy just above the K-absorption edge of Br at 13.475 kV where the photo-scattering cross section jumps by an order of magnitude. Such photon can be the Kα1 of Sr at 14.164 kV. But the Br photons are too soft for other than surface-located tissue; they cannot penetrate various parts of the body tissue. They can be used for superficially located tumors. In the method of the invention, therefore, heavier elements are generally preferred, with harder photons. Iodine, with its K-edge at 33.164 keV, would require much harder line-emission (from the Kα1 of La at 33.440 kV) to trigger its Auger emissions. Table 2 shows the energies of x-ray tube target elements in relation to the K-absorption energies of elements used to emit Auger electrons.

TABLE 2

Energies For Auger Generating Element and X-ray Tube Target

| Auger Element | K-absorption edge (ev) | X-ray Target | Emission Line (ev) |
|---|---|---|---|
| Calcium Ca | 4,038 | Scandium Sc | 4,090 (Kα$^1$) |
| | | | 4,085 (Kα$^2$) |
| Titanium Ti | 4,964 | Chromium Cr | 5,414 (Kα$^1$) |
| | | | 5,405 (Kα$^2$) |
| Bromine Br | 13,475 | Strontium Sr | 14,164 (Kα$^1$) |
| | | | 14,097 (Kα$^2$) |
| Iodine I | 33,164 | Lanthanum La | 33,440 (Kα$^1$) |
| Gadolium Gd | 50,229 | Thulium Tm | 50,730 (Kα$^1$) |

TABLE 2-continued

Energies For Auger Generating Element and X-ray Tube Target

| Auger Element | K-absorption edge (ev) | X-ray Target | Emission Line (ev) |
|---|---|---|---|
| Yttrium Y | 17,037 | Molybdenum Mo | 17,478 ($K\alpha^1$) |
|  |  |  | 17,373 ($K\alpha^2$) |
| Ruthenium Ru | 22,118 | Silver Ag | 22,162 ($K\alpha^1$) |

A gadolinium compound such as DTPA or $DO_3A$ may be used. Gd has a K-edge of 50.229 kV and can readily be excited by $K\alpha 1$ of Tm at 50.730 kV. As seen from FIG. 2, more than $10^6$ Gy can be delivered by the Auger electrons up to a distance of 10 Å.

The Functional X-Rays

Figure 3A:
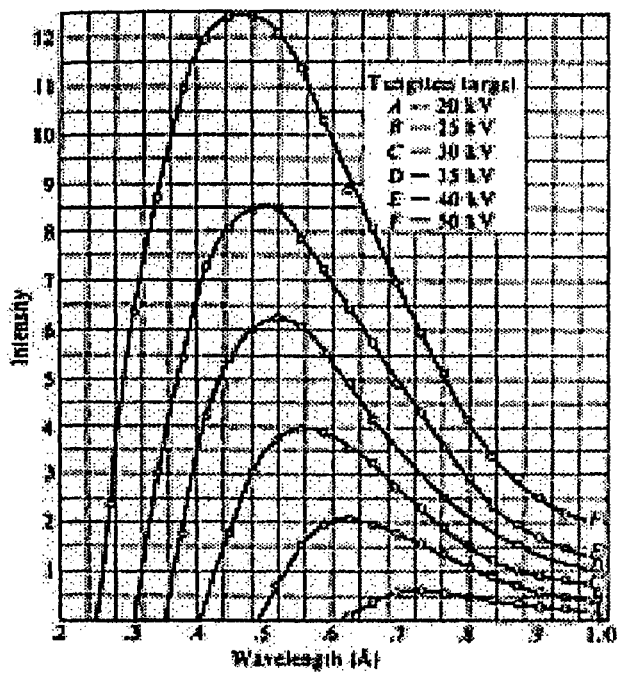
FIG. 3a is a graphical illustration of the spectrum of bremsstrahlung radiation.
Figure 3B:
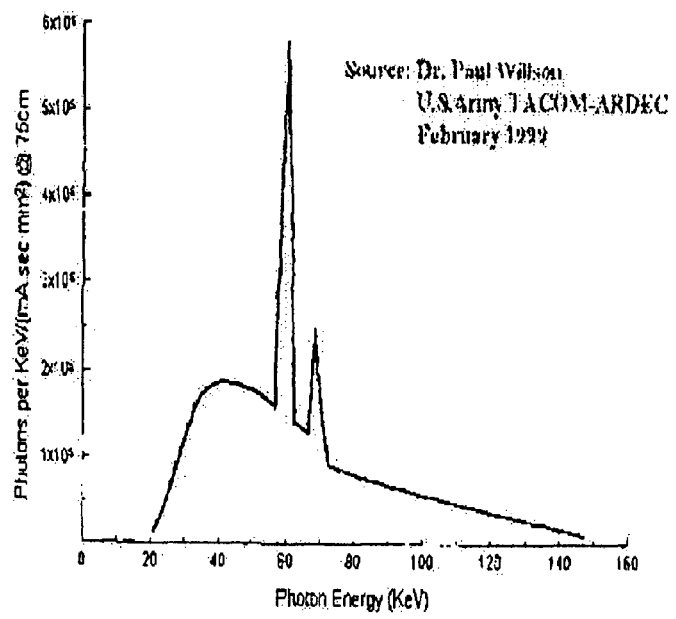
FIG. 3b is a graphical illustration of the spectrum of radiation emitted from a conventional side-window x-ray tube.

X-rays can be produced by synchrotron radiation or by an x-ray tube. The photon flux of a synchrotron drops by $E_p^{-4}$, with $E_p$ the photon energy, and renders the synchrotron ring useless for photon energies greater than 20 kV. X-ray tubes, on the other hand, become brighter as the photon flux $\sim E_e^{1.7}$, with $E_e$ the peak e-beam energy of the tube. Conventional x-ray tubes deliver x-rays with bremsstrahlung ("brem") which is the German word for "slow-down radiation". Brem basically have a continuum spectrum, as shown in FIG. 3a. Conventional x-rays are emitted at ~90° from the e-beam path, with higher voltage delivering harder photons and brighter flux. FIG. 3b shows the spectrum of a typical modern x-ray tube with high voltage e-beam and a solid tungsten target. The width of the tungsten line-emissions $K\alpha$ and $K\beta$, is the width of the detector resolution. A high resolution detector can reduce the line width by a factor of ten or more.

The x-ray photons from the conventional side-window x-ray tube can be used for imaging, or for radiation therapy, but they are not useful for the method of the present invention which requires delivery of line emission x-rays of a pre-selected energy.

Figure 4A:
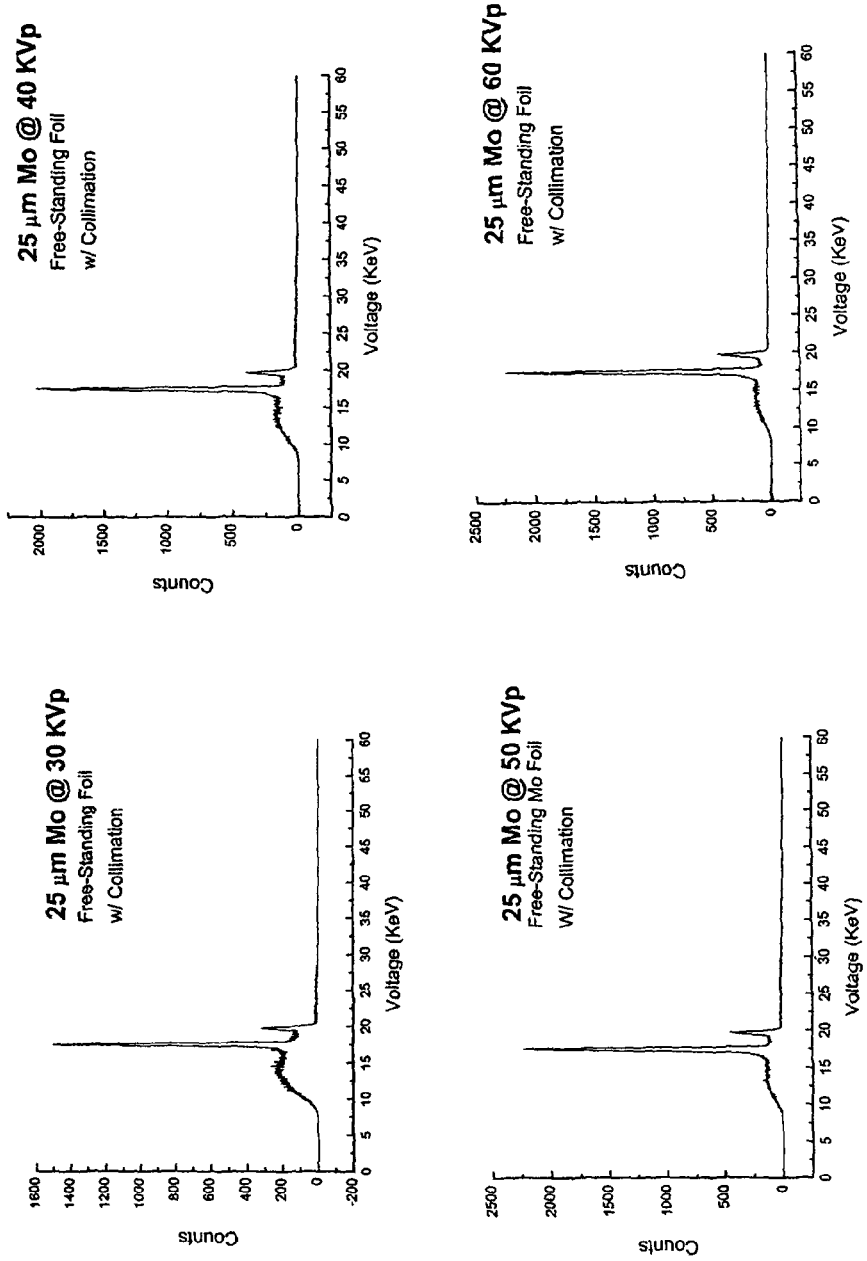
FIG. 4a depicts graphical spectra of radiation emitted from an end-window x-ray tube with a Mo target at different e-beam energies delivered to the target.
Figure 4B:
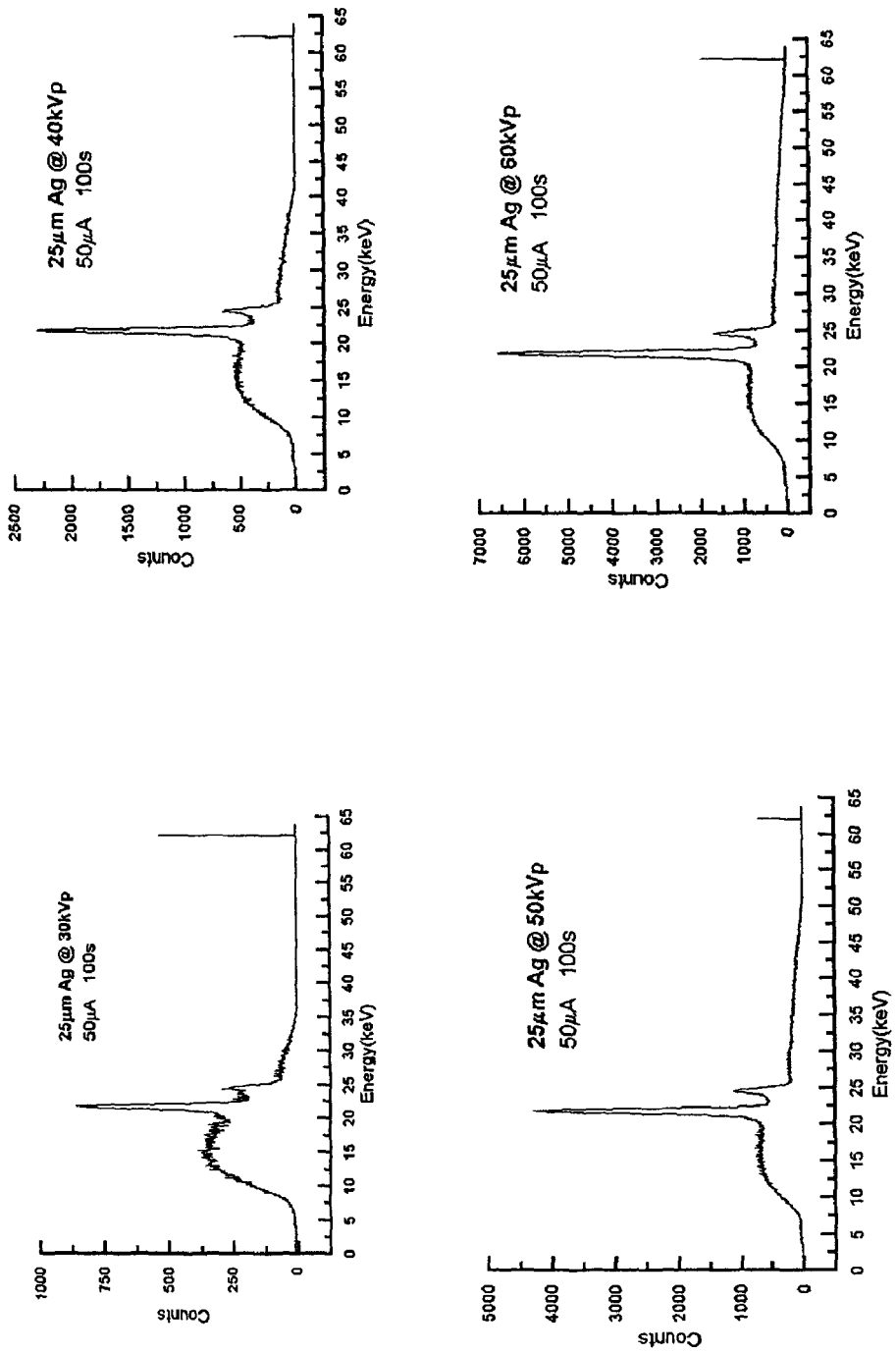
FIG. 4b depicts graphical spectra of radiation emitted from an end-window x-ray tube with a Ag target at different e-beam energies delivered to the target.
Figure 5:
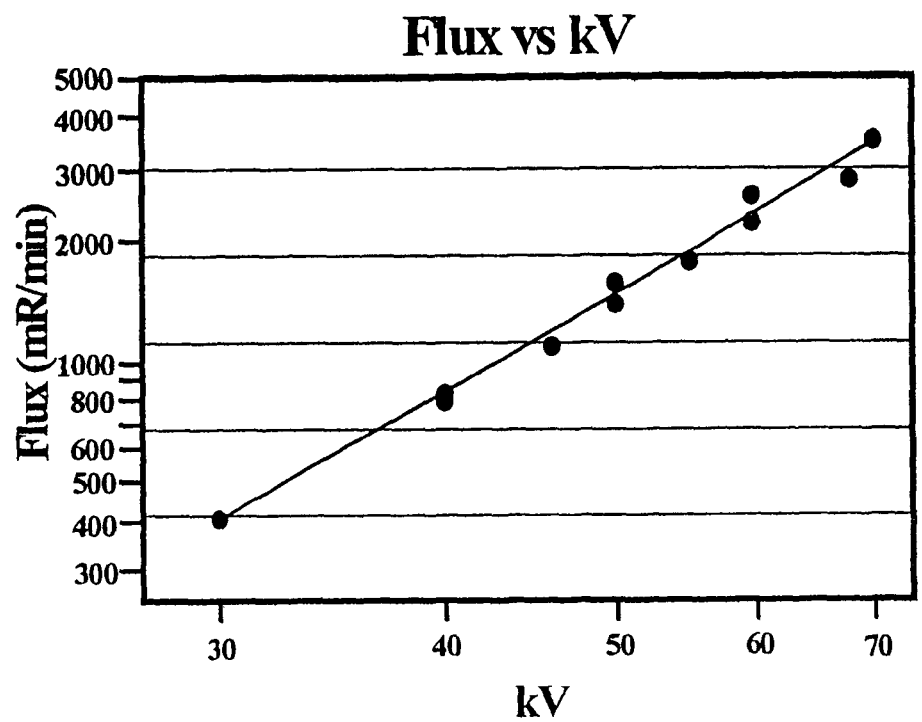
FIG. 5 is a graphical illustration of the relation between radiation flux and e-beam voltage for an end-window transmission x-ray tube.

Localized x-ray irradiation of elements, particularly heavy elements, in accordance with the invention may be done, for example, using an x-ray tube with an end-window target as described in above-mentioned U.S. Pat. No. 5,627,871. The tube is available from the assignee of the present applicant, NanoDynamics, Inc., 510 East 73$^{rd}$ Street, New York, N.Y. 10021. In use of this tube, the x-ray flux is delivered along the e-beam path and transmitted through the end-window. The x-ray target material is coated on a beryllium end-window which keeps the vacuum seal, conducts the current and the thermal load, and maintains the x-ray focal spot at a distance of only a fraction of one mm from the outside, or from the subject to be irradiated, if necessary. The e-beam is micro-focused on the transmission target, which is coated with a typical thickness of 10-20 μm. Electrons are stopped by the target metal within the first few microns or so, and the remaining target thickness functions as a filter, transforming the high energy beams to fluorescent line-emissions characteristic of the target element. FIG. 4a shows the emission spectrum of an end-window molybdenum target and FIG. 4b shows the spectrum of an end-window silver target. It is of interest to note that as the e-beam energy varies from 30 kV to 60 kV, the emission spectrum simply becomes "cleaner and purer", with mainly the fluorescent K-emissions of the target. A careful examination of the spectra shown in FIGS. 4a and 4b indicates that most of the x-ray flux is concentrated in the line-emissions. These emissions can be used for the functional irradiation to excite the compounded element from which the induced Augers will cause the desired DNA disruption. Also, the end-window target design not only provides a photon flux with a mostly monochromatic spectrum, but the total x-ray flux is also much brighter than with conventional tubes. FIG. 5 shows the flux versus applied voltage, or flux $\sim E_e^{2.5}$ as compared to the conventional tube brightness with flux $\sim E_e^{1.7}$. This added brightness is due to the fact that the transmission target design can take advantage of making use of the radiation along the e-beam path, which is favored by the forward relativistic transform of the dipole radiation at higher e-beam energies. This forward radiation is buried in the solid target in a conventional x-ray tube.

Figure 6:
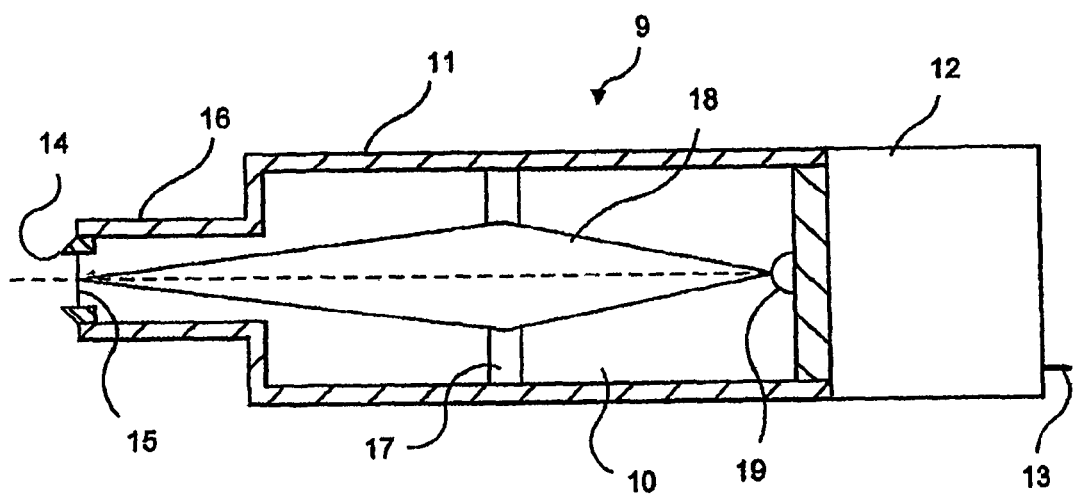
FIG. 6 is a schematic elevational view partly in cross-section of a compact end-window transmission x-ray tube useful in the present invention, taken from the above-mentioned U.S. Pat. No. 5,627,871.

FIG. 6 illustrates the above-mentioned end window x-ray tube integrated with a high voltage power supply. In FIG. 6, x-ray tube 9 comprises an evacuated tubular chamber 10 enclosed by a tubular ceramic envelope 11. At one end chamber 10 is connected to end window 14. At its other end, chamber 10 is connected to a power supply 12 which is connected by line 13 to an electrical current supply, not shown, such as a 120 V AC outlet. The power supply may be adjusted so that the energy of x-ray photons from the tube ranges up to 100 KV. Power supply 12 comprises transformers and circuit elements for supplying current to an emitter 19 and to electrostatic lens 17. The components of power supply 12 are contained in a housing which may be made of plastic or metal, and said housing may be filled with an insulating oil or gel.

End window 14 has on its inside surface a metal foil target 15. The end window may be mounted in a tubular extension 16 of smaller diameter than ceramic envelope 11. Tubular extension 16 may be ceramic or metal, is usually stainless steel and, being open to the interior of chamber 10, is evacuated. A typical outside diameter of tubular extension 16 is ⅝ inch. Tubular extension 16 may be surrounded by an annular magnetic coil or lens (not shown). Within chamber 10 is at least one electrostatic lens 17 which focuses e-beam 18.

Contained in chamber 10 is e-beam emitter 19 connected to said power supply 12. The e-beam emitter 19 may comprise a whisker such as a whisker of a tungsten filament. The whisker may have a diameter of several microns and a chemically etched tip of submicron size, from which e-beam 19 is generated. The e-beam is focused by electrostatic focusing 17. Further focusing may be accomplished by the above-mentioned magnetic lens.

Because of the much higher quantum efficiency of producing x-rays along the e-beam path, a small power supply shown in FIG. 6 delivers an x-ray flux as bright as that of a typical mammography instrument, yet it has less than ⅒ of the weight and size.

Chelating Agents and Gd Chelates

The following are useful chelating agents:

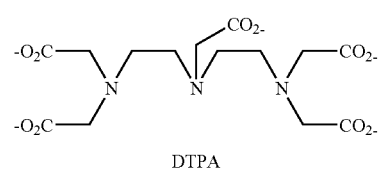

DTPA

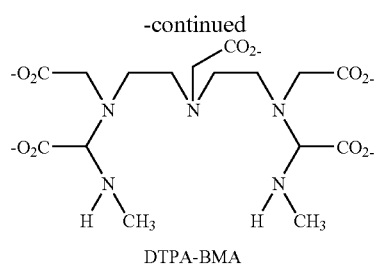

DTPA-BMA

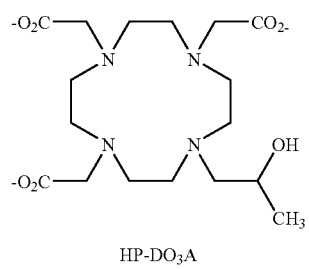

HP-DO$_3$A

Gadolinium contrast agents are widely used in MRI for applications such as the evaluation of inflammatory conditions and the visualization of cancerous lesions. Due to the typically increased and "leaky" vascularity of tumors compared to normal tissue, Gd agents leak into and pool in the extracellular spaces of such cancerous tissue. Gd is a rare element which has seven unpaired electrons when combined in compounds, making it highly paramagnetic. The resulting T1 and T2 relaxtivity effects of Gd on its local environment creates an increased MRI signal intensity and allows clear visualization of the tumor distribution. Standard T1 weighted imaging sequences are typically employed to observe this enhancement.

Free Gd ion in itself is toxic and needs to be strongly chelated to render it safe for clinical use. Gd-DTPA (Magnevist; Berlex) was the first U.S. FDA approved contrast agent for MRI. It has been administered to over 20 million patients with an excellent safety record. Subsequently, other chelated Gd compounds have been FDA approved for clinical use, including Gd-DO$_3$A (ProHance; Bracco Diagnostics) and Gd-DTPA-BMA (Omniscan; Nycomed). The standard dosage of these Gd chelates is 0.1 mmol/kg; however, for the latter two agents, up to 0.3 mmol/kg can be administered. The reported LD$_{50}$ in mice for Gd-DTPA is ~10 mmol/kg.

The GD chelates are excreted through normal glomerular filtration, and have a serum half life of approximately 90 minutes. One week following administration, less than 0.5% of the injected dose has been measured in the circulation. On the other hand, the free Gd ion is only slowly excreted by the kidney and remains in the body a long time. Since free Gd is toxic, Gd-chelate dissociation, either due to transmetallation or otherwise is of concern. The kinetic [k(obs)s$^{-1}$] and thermodynamic equilibrium (log K$_{eg}$) stability contrasts are listed in Table 3 for the three above mentioned Gd compounds.

TABLE 3

| AGENT | Log K$_{eg}$ | K(obs)s$^{-1}$ |
|---|---|---|
| Gd-DTPA | 22.2 | $1.2 \times 10^{-3}$ |
| Gd-DO$_3$ | 23.8 | $6.3 \times 10^{-5}$ |
| Gd-DTPA-BMA | 16.9 | $>2 \times 10^{-2}$ |

Gd-containing Complexes

Complexes of Gd-DTPA can be made and have been done so since the mid-1980's. The impetus for such molecules was the development of MRI contrasting agents that exhibited a preferential biological distribution (Ogan et al., Invest Radiol 22, 665; 1987). This work led to the development of Gd-DTPA-albumin and Gd-DTPA-polyamine as well as other derivatives more recently. These molecules "are retained in the vasculature longer than conventional small molecular contrast agents", and "have been developed to visualize the blood pool, tissue blood volume, and small vasculature" (Sato et al., 2001). It appears that Gd-DTPA derivatives are usually generated by conjugating the new moiety to DTPA or to a DTPA containing salt (such as Gd-nitrioltriacetic acid), permitting an exchange reaction and chelation of the Gd by DTPA. The resulting Gd-DTPA-conjugate is purified by dialysis (Ogenet et al., 1987; Sato et al.; Magn Resn in Med 46 1169, 2001).

Besides Gd-DTPA, Gd can be conjugated with other molecules. Increasing the size of the complex increases tissue retention time and decreases kidney-mediated excretion rate. Since there is a constant, low-level release of free gadolinium ion from the chelated form, and free Gd ion is toxic, this is not desirable. Thus, it is important that the clearance rate remain high and the size of the conjugate is not that big.

The chemotherapeutic agent may be linked to the carrier compound by conjugation or chemical bonds which are susceptible to being broken by ionizing radiation. For example, the chemotherapeutic compound may be coupled to a chelating agent such as DTPA covalently through a reactive carboxyl group on DTPA and, normally, a bifunctional linker on the chemotherapeutic compound to be coupled. A pre-selected element such as Gd is then added for chelation by the modified DTPA and purified by dialysis.

EXAMPLE

Preparation of Transfer Compound by Coupling to Gd-containing Complex

Synthesis of 7-DTPA-Paclitaxel can be achieved by mixing diethylenetriaminepentacetic acid anhydride (DTPA-A) and paclitaxel (taxol) in dry dimethylformamide (DMF) and retain much of the paclitaxel potency in the cells (Chan Li et al., J. Nuc. Med. 38, 1042; July, 1997). Upon coupling of DTPA and taxol, the chelating of gadolinium can simply be the adding of a Gd salt such as gadolinium nitrioltriacetic acid. The exchange/chelation reaction is apparently spontaneous.

Rose Bengal

Another compound which may be used in the present invention is rose bengal.

Rose Bengal is a xanthine derivative, a modified form of fluorescein, containing four chlorines and four iodines with a total molecular weight of 1017.65. It is also known as Acid Red 94 and Food Red 105. It's full chemical name is: 9-(3', 4',5',6'-tetrachloro-O-carboxyphenyl)-6-hydroxy-2,4,5,7-tetraiodo-3-isoxanthone 2Na or 4,5,6,7-Tetrachloro-2',4',5', 7'-tetraiodofluorescein disodium salt.

Its structure is shown as follows:

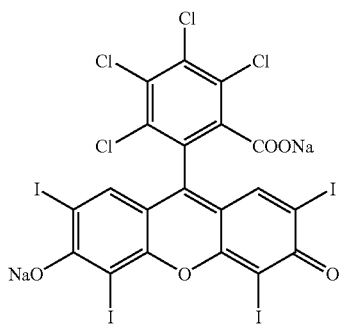

Rose bengal has many uses. In association with chloramphenicol it is used in a selective agar medium for the isolation of slow growing fungal contaminants in food. In the medical field it is used as a test for "dry eye" where the compound is taken up by devitalized epithelial cells. Positive staining of the conjuctiva with rose bengal is consistent with a diagnosis of dry eye syndrome.

I 131-labeled rose bengal is used as a test of liver function as a means of measuring hepatic blood flow and for scintillation scanning of the liver to determine size and contour of the liver, or the presence of space occupying masses in the liver. Of specific interest is its use in photooxidative therapy. Light causes the production of a triplet state which then reacts with molecular oxygen in the ground state to produce singlet oxygen species. Rose bengal accumulates in the cytoplasm of cells, particularly in lysosomes. Lysosomes contain a number of hydrolytic enzymes capable of breaking down proteins and certain carbohydrates. Shining light on such cells leads to significant oxidative damage which leads to disruption of the lysosomes and cell death. With four iodine atoms per molecule of rose bengal, the use of line emission x-rays tuned to iodine (i.e. from a lanthanum target end window transmission x-ray tube (as described herein) will lead to a massive Auger cascade and disruption of the lysosomes and cell death. The clear advantage of the use of x-rays is the increased tissue penetration when compared with light activation.

Rose bengal is used without needing to be complexed with a carrier compound since rose bengal itself contains elements, i.e. iodine, which can be irradiated to cause emission of Auger electrons. It may be administered e.g. orally or by injection.

Irradiation of specific tumor locations localizes cell damage. A tumor selective effect also can be employed. Rose bengal will be excreted or metabolized earlier from normal tissues than from tumorous tissues. Therefore, timing the irradiation to occur after a selected interval from the time of administration, e.g. 12 to 24 hours, will take advantage of the tumor specific effect.

The invention claimed is:

1. A method for preferential destruction of tumor cells in a subject, the method comprising the steps of:
   (a) administering rose bengal to the subject such that the rose bengal accumulates in lysosomes of cells of the subject; and then
   (b) irradiating a specific location of the subject comprising a tumor with an x-ray tube that emits monochromatic line emission x-rays having an energy above and near the K-absorption edge or the L-absorption edge of iodine that is present in the rose bengal so as to cause emission of Auger electrons from the rose bengal accumulated in the lysosomes of irradiated cells, wherein the emission of Auger electrons is in a dose effective to cause disruption of the lysosomes with release of hydrolytic enzymes in the lysosomes and death of said irradiated cells in the specific location, said dose being at least $10^6$ Gy within a distance of up to 10 Angstroms from the iodine in the rose bengal, said irradiating being confined to the specific location comprising the tumor so as to localize damage caused by the irradiating and to minimize damage to normal cells of the subject.

2. The method according to claim 1, wherein the subject is a human.

3. The method according to claim 1, wherein the x-ray tube has a target that is lanthanum.

4. The method according to claim 1, wherein the irradiating in step (b) is performed at least 12 hours after the administering of rose bengal in step (a).

5. The method according to claim 1, wherein the irradiating in step (b) is performed from 12-24 hours after the administering of rose bengal in step (a).

6. The method according to claim 1, wherein the rose bengal is administered to the subject orally.

7. The method according to claim 1, wherein the rose bengal is administered to the subject intravenously.

8. The method according to claim 1, wherein the rose bengal is administered to the subject enterically.

9. The method according to claim 1, wherein the specific location predominantly contains tumor cells.

10. The method according to claim 1, wherein the rose bengal is administered directly to a specific organ or tissue of the subject containing tumor cells.

11. The method according to claim 1, wherein the tumor comprises tumorous tissue and the irradiating is performed with the rose bengal present in the tumorous tissue in a greater concentration than in normal tissue of the subject.

12. The method according to claim 11, wherein the irradiating is performed at least 12 hours after the administering of the rose bengal.

13. The method according to claim 12, wherein the irradiating is performed from 12-24 hours after the administering of the rose bengal.

14. In a method for treating tumors with x-ray radiation comprising the steps of (i) delivering into a tumor a compound that enhances an effect of x-rays upon irradiation of the tumor and then (ii) irradiating the tumor containing the compound with the x-rays, the improvement wherein the compound delivered to the tumor is rose bengal, which accumulates in lysosomes of cells, and wherein the irradiating is performed with an x-ray tube that emits monochromatic line emission x-rays having an energy above and near the K-absorption edge or the L-absorption edge of iodine that is present in the rose bengal so as to cause emission of Auger electrons from the rose bengal accumulated in the lysosomes of irradiated cells in a dose effective to cause disruption of the lysosomes and death of the irradiated cells, said dose being at least $10^6$ Gy within a distance of up to 10 Angstroms from the iodine in the rose bengal, said irradiating being directed to a specific tumor location comprising tumor cells so as to localize damage caused by the irradiating and to minimize damage to healthy cells.

15. The method according to claim 14, wherein the specific tumor location predominantly contains the tumor cells.

16. The method according to claim 14, wherein the rose bengal is administered to a tissue or organ removed from the body of a subject.

17. The method according to claim 14, wherein the rose bengal is administered directly to a specific organ or tissue of a subject containing the tumor cells.

18. The method according to claim 14, wherein the specific tumor location comprises tumorous tissue of a subject and the irradiating is performed with the rose bengal being present in the tumorous tissue in a greater concentration than in normal tissue of the subject.

19. The method according to claim 18, wherein the irradiating is performed at least 12 hours after the administering of the rose bengal.

20. The method according to claim 18, wherein the irradiating is performed from 12-24 hours after the administering of the rose bengal.

* * * * *